United States Patent

Gaffar et al.

[11] Patent Number: 5,094,844
[45] Date of Patent: Mar. 10, 1992

[54] ANTICALCULUS ORAL COMPOSITION

[75] Inventors: Abdul Gaffar, Princeton; John Afflitto, Brookside; Sahar F. Smith, Bordentown, all of N.J.

[73] Assignee: Colgate-Palmolive Company, Piscataway, N.J.

[21] Appl. No.: 631,302

[22] Filed: Dec. 20, 1990

[51] Int. Cl.$^5$ .......................... A61K 7/16; A61K 7/18
[52] U.S. Cl. .......................................... 424/52; 424/57
[58] Field of Search ...................... 424/49–88, 424/52, 57

[56] References Cited

U.S. PATENT DOCUMENTS

| | | | |
|---|---|---|---|
| 3,429,963 | 2/1969 | Shedlovsky | 424/56 |
| 4,138,477 | 2/1979 | Gaffar | 424/52 |
| 4,427,652 | 1/1984 | Gaffar | 424/52 |
| 4,816,245 | 3/1989 | Gaffar | 424/57 |
| 4,877,603 | 10/1989 | Degenhardt et al. | 424/57 |

FOREIGN PATENT DOCUMENTS 2224204  2/1990  United Kingdom ................. 424/57

OTHER PUBLICATIONS

Anbar C.A. 82 #25739d (1974).
Anbar, C.A. 82 #164761t (1974).
Gaffar, C. A. 103 #183398y (1985).
Gaffar, C.A. 107 #120079u (1986).
Gaffar, C.A. 113 #158473t (1990).

*Primary Examiner*—Shep K. Rose
*Attorney, Agent, or Firm*—Robert L. Stone; Murray M. Grill

[57] ABSTRACT

An oral composition such as a toothpaste (including gel or cream), mouthwash, lozenge, chewing gum or tooth powder containing a calculus-inhibiting amount of a linear molecularly dehydrated polyphosphate salt and, as inhibitor of enzymatic hydrolysis of said polyphosphate salt in saliva, a synthetic polymeric vinyl phosphate. A fluoride-ion providing source may also be present to further inhibit the enzymatic hydrolysis of said polyphosphate salt.

19 Claims, No Drawings

ANTICALCULUS ORAL COMPOSITION

This invention relates to oral compositions containing an anticalculus agent.

Calculus is a hard, mineralized formation which forms on the teeth. Regular brushing aids in preventing a rapid buildup of these deposits, but even regular brushing is not sufficient to remove all of the calculus deposits which adhere to the teeth. Calculus is formed on the teeth when crystals of calcium phosphates begin to be deposited in the pellicle and extracellular matrix of the dental plaque and become sufficiently closely packed together for the aggregates to become resistant to deformation. There is no complete agreement on the route by which calcium and orthophosphate ultimately become the crystalline material called hydroxyapatite (HAP). It is generally agreed, however, that at higher saturations, that is, above the critical saturation limit, the precursor to crystalline HAP is an amorphous or microcrystalline calcium phosphate. "Amorphous calcium phosphate" although related to hydroxyapatite differs from it in atomic structure, particle morphology, and stoichiometry. The X-ray diffraction pattern of amorphous calcium phosphate shows broad peaks typical of amorphous materials, which lack the long-range atomic order characteristic of all crystalline materials, including HAP. It is apparent, therefore, that agents which effectively interfere with crystalline growth of HAP will be effective as anticalculus agents. A suggested mechanism by which the anticalculus agents of this invention inhibit calculus formation probably involves an increase of the activation energy barrier, thus inhibiting the transformation of precursor amorphous calcium phosphate to HAP.

Studies have shown that there is a good correlation between the ability of a compound to prevent HAP crystalline growth in vitro and its ability to prevent calcification in vivo, provided of course that such compound is stable in and inert to saliva and its components.

It is well known in the art that water soluble hexametaphosphates, tripolyphosphates and pyrophosphates and the like are effective calcium and magnesium ion suppressors, inhibitors, sequestrants and/or chelating agents, and are effective inhibitors of HAP formation in vitro. U.S. Pat. No. 4,515,772 issued May 7, 1985, to Parran et al discloses and claims oral anticalculus compositions containing a fluoride ion source and soluble dialkali metal pyrophosphates. The voluminous number of acknowledged prior art and "References Cited" in this patent indicate the many uses and functions of polyphosphates hitherto proposed in oral compositions.

However, as in part admitted in the aforesaid patent disclosure and as shown hereinafter in U.S. Pat. No. 4,627,877, issued Dec. 9, 1986, to Gaffar et al as well as and in U.S. Pat. No. 4,806,340, issued Feb. 21, 1989, to Gaffar et al, the linear molecularly dehydrated polyphosphates (i.e. hexametaphosphates, tripolyphosphates, pyrophosphates, etc.) in common, when introduced into the oral cavity and/or saliva are significantly hydrolyzed by salivary enzymes (phosphatase) to orthophosphates which are ineffective as inhibitors of HAP formation.

In U.S. Pat. Nos. 4,627,977 and 4,806,340, the use of polymeric polycarboxylate and of a fluoride ion-source was taught to successfully overcome the hydrolysis of the linear molecularly dehydrated polyphosphate anticalculus agents by salivary phosphatase. Thus, polycarboxylate inhibits pyrophosphate hydrolyses by alkaline phosphatase; the fluoride-ion source inhibits of pyrophosphate hydrolysis by acid phosphatase and pyrophosphatase.

It is the object of the present invention to even more effectively inhibit the action of salivary enzymes on polyphosphate anticalculus agents with a non-polycarboxylate polymer.

A further object of the invention is to provide an oral composition which inhibits the transformation of amorphous calcium phosphate to HAP crystal structure normally associated with calculus.

Another object of this invention is the provision of an improved method for inhibiting the formation of calculus.

Other objects and advantages will appear as the description process.

In accordance with certain of its aspects, this invention relates to an oral composition containing, in an orally acceptable vehicle an effective anticalculus amount of at least one linear molecularly dehydrated polyphosphate salt as essential anticalculus agent, and, an effective amount of inhibitor against enzymatic hydrolysis of said agent in saliva up to about 4% of a synthetic anionic polyvinyl phosphonate, having recurring groups

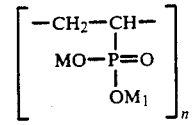

and average molecular weight of about 1,000 and greater; wherein M and $M_1$ are hydrogen, alkali metal or ammonium, and wherein M and $M_1$ are the same or different.

Molecular weight values given for such polyvinyl phosphonates are obtained from viscosity or light scattering measurements.

Synthetic anionic polyvinyl phosphonates have been previously disclosed as anticalculus agents per se in, U.S. Pat. No. 3,429,963 to Shedlovsky. However, that patent does not disclose use of such polyvinyl phosphonate agent for inhibiting salivary hydrolysis of linear polyphosphates.

The linear molecularly dehydrated polyphosphate salts, such as hexametaphosphates, tripolyphosphates and pyrophosphates, which are operative herein as anticalculus agents are well known, being generally employed in the form of their wholly or partially neutralized water soluble alkali metal (e.g. potassium or sodium) or ammonium salts, and any mixtures thereof. Representative examples include sodium hexametaphosphate, sodium tripolyphosphate, disodium diacid pyrophosphate, trisodium monoacid pyrophosphate and tetrasodium pyrophosphate and the like; for instance the linear molecularly dehydrated polyphosphates may contain about 2 to 125 phosphorus atoms. They are generally employed in the instant oral compositions in approximate weight amounts of about 0.1 to 7% preferably about 2 to 6%. As previously indicated, these salts are disclosed as anticalculus agents in U.S. Pat. Nos. 4,627,977 and 4,806,340.

When pyrophosphate salt is employed it is preferred to use a mixture of tetrapotassium pyrophosphate and tetrasodium pyrophosphate, with tetrapotassium pyrophosphate being in predominant amount. When only tetrasodium pyrophosphate is employed, some can remain undissolved, thereby rendering the oral composition gritty in appearance and feel. Thus, when a preferred combination of about 4.3-7% by weight of a mixture of tetrapotassium pyrophosphate and tetrasodium pyrophosphate is employed, the tetrapotassium pyrophosphate salt is in predominant amount and grittiness is substantially reduced. Preferred ratios of the tetrapotassium-tetrasodium salts range from about 4.3:2.7 to about 6:1, especially a ratio of 4.5:1.5. There may be desirably present about 4.3% to about 7% of tetrapotassium pyrophosphate alone or with up to 2.7% of tetrasodium pyrophosphate. In an alternative preferred embodiment lesser effective anticalculus amounts of tetrasodium pyrophosphate, such as about 0.1-2% by weight are employed and effectively dissolved. An aspect of the invention also includes the presence of, dialkali metal pyrophosphate, for instance in amount of about 0.1% to about 0.4% or about 1.0% by weight if desired.

The polyvinylphosphonate may be present as in its water-soluble acid form, or salt (including acid salts) form. Salts include the alkali metal, preferably sodium or potassium, or ammonium water-soluble salts. The polymer has an average molecular weight of at least about 1,000, typically about 1,000 to about 1,000,000 and most preferably about 6,000 to about 100,000. It may be polymerized from vinyl phosphonyl chloride by free radical polymerization in accordance with art recognized technique. The polyvinyl phosphonate is employed in amount effective to inhibit enzymatic salivary hydrolysis of the linear molecularly dehydrated polyphosphate in amount up to about 4% by weight. It is generally employed in the compositions in approximate weight amounts of 0.05 to 4%, generally about 0.05 to 3%, preferably 0.05 to 2%, more preferably 0.1 to 2% by weight. Amounts of at least about 1% by weight are typically employed in dentifrice compositions, meaning oral compositions generally containing a dental abrasive and used in conjunction with brushing of the teeth, e.g. tooth pastes including gels and creams, and powders. Amounts in excess of 4% by weight may be employed for thickening or gelling purposes.

In addition to the polyvinyl phosphonate inhibitor of polyphosphate hydrolysis by the alkaline phosphatase salivary enzymes, additional hydrolysis inhibition is attained by the presence of a fluoride-ion source to inhibit hydrolysis by acid phosphatase and pyrophosphatase salivary enzymes. This material is preferably present and also serves to reduce caries formation.

The source of fluoride ions, or fluorine-providing compounds, which may be present as a combination enzyme inhibitor, are well known in the art as anti-caries agents and also act as such agents in the practice of this invention. These compounds may be slightly soluble in water or may be fully water-soluble. They are characterized by their ability to release fluoride ions in water and by freedom from undesired reaction with other compounds of the oral preparation. Among these materials are inorganic fluoride salts, such as soluble alkali metal, alkaline earth metal salts, for example, sodium fluoride, potassium fluoride, ammonium fluoride, calcium fluoride, a copper fluoride such as cuprous fluoride, zinc fluoride, barium fluoride, sodium fluosilicate, ammonium fluorosilicate, sodium fluorozirconate, sodium monofluorophosphate, aluminum mono-and di-fluorophosphate, and fluorinated sodium calcium pyrophosphate. Tin fluorides and particularly alkali metal fluorides, such as sodium fluoride and alkali metal monofluorophosphate (MFP), such as sodium MFP and mixtures thereof, are preferred.

The amount of fluorine-providing compound, when present, is dependent to some extent upon the type of compound, its solubility, and the type of oral preparation, but it must be a nontoxic amount, generally about 0.005 to about 3.0% in the preparation. In a dentifrice preparation, e.g. gel, cream, toothpaste or toothpowder, an amount of such compound which releases up to about 2,000 ppm of F ion by weight of the preparation is considered satisfactory. Any suitable minimum amount of such compound may be used, but it is preferable to employ sufficient compound to release about 300 to about 2,000 ppm. more preferably about 800 to about 1,500 ppm of fluoride ion. Typically, in the cases of alkali metal fluorides and stannous fluoride, this component is present in an amount up to about 2% by weight, based on the weight of the preparation, and preferably in the range of about 0.05% to 1%. In the case of sodium monofluorophosphate, the compound may be present in an amount of about 0.1-3%, more typically about 0.76%.

In oral preparations such as mouthwashes, lozenges and chewing gum, the fluorine-providing compound, when present, is typically present in an amount sufficient to release up to about 500 ppm, preferably about 25 to about 300 ppm by weight of fluoride ion. Generally about 0.005 to about 1.0 wt. % of such compound is present.

In certain highly preferred forms of the invention the oral composition may be substantially liquid in character, such as a mouthwash or rinse. In such a preparation, the vehicle is typically a water-alcohol mixture desirably including a humectant as described below. Generally, the weight ratio of water to alcohol is in the range of from about 1:1 to about 20:1, preferably about 2:1 to 10:1 and more preferably about 4:1 to about 6:1. The total amount of water-alcohol mixture in this type of preparation is typically in the range of from about 70% to about 99.9% by weight of the preparation.

The pH of such liquid and other preparations of the invention is generally in the range of from about 4.5 to about 9 and typically from about 5.5 to 8. The pH is preferably in the range of from about 6 to about 8.0. It is noteworthy that the compositions of the invention may be applied orally at a pH below 5 without substantially decalcifying or otherwise damaging dental enamel. The pH can be controlled with acid (e.g. citric acid or benzoic acid) or base (e.g. sodium hydroxide) or buffered (as with sodium citrate, benzoate, carbonate, or bicarbonate, disodium hydrogen phosphate, sodium dihydrogen phosphate, etc.).

In certain other desirable forms of this invention, the oral composition may be substantially solid or pasty in character, such as toothpowder, a dental tablet or a toothpaste (including gel or dental cream). The vehicle of such solid or pasty oral preparation generally contains a dentally acceptable water-insoluble polishing material. Examples of polishing materials are water-insoluble sodium metaphosphate, potassium metaphosphate, tricalcium phosphate, dihydrated dicalcium phosphate, anhydrous dicalcium phosphate, calcium pyrophosphate, magnesium orthophosphate, trimagnesium phosphate, calcium carbonate, aluminum silicate, zirconium silicate, siliceous polishing agent, bentonite, and mixtures thereof. Other suitable polishing materials include the particulate thermosetting resins described in U.S. Pat. No. 3,070,510 of Dec. 15, 1962 such as melamine-, phenolic-, and ureaformaldehydes, and crosslinked polyepoxides and polyesters. Preferred polishing materials include crystalline silica having particle sizes of up to about 5 microns, a mean particle size of up to about 1.1 microns, and a surface area of up to about 50,000 $cm^2/gm.$, silica gel or colloidal silica, and complex amorphous alkali metal aluminosilicate.

When visually clear, translucent or opacified gels are employed a siliceous polishing agent of colloidal silica, such as those sold under the trademark SYLOID as Syloid 72 and Syloid 74, Zeodent as Zeodent 113 and Zeodent 115 or under the trademark SANTOCEL as Santocel 100 and alkali metal alumino-silicate complexes or silica containing combined alumina, such as Zeo 49A or Zeo 49B, are particularly useful, since they have refractive indices close to the water and/or humectant) systems commonly used in dentifrices.

Many of the so-called "water-insoluble" polishing materials are anionic in character and also include small amounts of soluble material. Thus, insoluble sodium metaphosphate may be formed in any suitable manner as illustrated by Thorpe's Dictionary of Applied Chemistry, Volume 9, 4th Edition, pp. 510-511. The forms of insoluble sodium metaphosphate known as Madrell's salt and Kurrol's salt are further examples of suitable materials. These metaphosphate salts exhibit only a minute solubility in water, and therefore are commonly referred to as insoluble metaphosphates (IMP). There is present therein a minor amount of soluble phosphate material as impurities, usually a few percent such as up to 4% by weight. The amount of soluble phosphate material, which is believed to include a soluble sodium trimetaphosphate in the case of insoluble metaphosphate, may be reduced or eliminated by washing with water if desired. The insoluble alkali metal metaphosphate is typically employed in powder form of a particle size such that no more than about 1% of the material is larger than about 37 microns.

The polishing material is generally present in the solid or pasty compositions in weight concentrations of about 10% to about 99%. Preferably, it is present in amounts ranging from about 10% to about 75% in toothpaste, and from about 70% to about 99% in toothpowder.

In a toothpaste, the liquid vehicle may comprise water and humectant typically in an amount ranging from about 10% to about 90% by weight of the preparation. Glycerine, propylene glycol, sorbitol, polypropylene glycol and/or polyethylene glycol (e.g. 400-600) exemplify suitable humectant carriers. Also advantageous are liquid mixtures of water, glycerine and sorbitol. In clear gels where the refractive index is an important consideration, about 3-30 wt. % of water, 0 to about 80 wt. % of glycerine, and about 20-80 wt. % of sorbitol is preferably employed.

Toothpastes (including creams and gels) typically contain a natural or synthetic thickener or gelling agent in proportions of about 0.1% to about 10%, preferably about 0.5% to about 5% by weight. A suitable thickener is synthetic hectorite, a synthetic colloidal magnesium alkali metal silicate complex clay available for example as Laponite (e.g. CP, SP 2002, D) marketed by Laporte Industries Limited. Laponite D analysis shows, approximately by weight, 58.00% $SiO_2$, 25.40% MgO, 3.05% $Na_2O$, 0.98% $Li_2O$ and some water and trace metals. Its true specific gravity is 2.53 and it has an apparent bulk density (g./ml. at 8% moisture) of 1.0.

Other suitable gelling agents include Irish moss, gum tragacanth, starch, polyvinylpyrrolidone, hydroxyethyl propylcellulose, hydroxybutyl methyl cellulose, hydroxypropyl methyl cellulose, hydroxyethyl cellulose (e.g. available as Natrosol), sodium carboxymethyl cellulose, xanthan and colloidal silica such as finely ground Syloid (e.g. 244). As mentioned earlier, the synthetic anionic polyvinyl phosphonate can also provide thickening or gelling properties. Colloidal silica such as finely ground Syloid (e.g. 244) is also a suitable thickener.

It will be understood that, as is conventional, the oral preparations are to be sold or otherwise distributed in suitable labelled packages. Thus a jar of mouthrinse will have a label describing it, in substance, as a mouthrinse or mouthwash and having directions for its use; and a toothpaste, cream or gel will usually be in a collapsible tube, typically aluminum, lined lead or plastic, or other squeeze, pump or pressurized dispenser for metering out the contents, having a label describing it, in substance, as a toothpaste, gel or dental cream.

Organic surface-active agents are used in the compositions of the present invention to achieve increased prophylactic action, assist in achieving thorough and complete dispersion of the anticalculus agent throughout the oral cavity, and render the instant compositions more cosmetically acceptable. The organic surface-active material is preferably anionic, nonionic or ampholytic in nature, and it is preferred to employ as the surface-active agent a detersive material which imparts to the composition detersive and foaming properties. Suitable examples of anionic surfactants are water-soluble salts of higher fatty acid monoglyceride monosulfates, such as the sodium salt of the monosulfated monoglyceride of hydrogenated coconut oil fatty acids, higher alkyl sulfoacetates higher fatty acid esters of 1,2 dihydroxy propane sulfonate, and the substantially saturated higher aliphatic acyl amides of lower aliphatic amino carboxylic acid compounds such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine which should be substantially free from soap or similar higher fatty acid material. The use of these sarcosinate compounds in the oral compositions of the present invention is particularly advantageous since these materials exhibit a prolonged and marked effect in the inhibition of acid formation in the oral cavity due to carbohydrate breakdown in addition to exerting some reduction in the solubility of tooth enamel in acid solutions. Examples of water-soluble nonionic surfactants are condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of poly(ethylene oxide) with fatty acids, fatty alcohols, fatty amides, polyhydric alcohols (e.g. sorbitan monostearate) and polypropyleneoxide (e.g. block copolymer Pluronic materials).

Various other materials may be incorporated in the oral preparations of this invention such as whitening agents, preservatives, silicones, chlorophyll compounds, other anticalculus agents, and/or ammoniated material such as urea, diammonium phosphate, and mixtures thereof. These adjuvants, where present, are incorporated in the preparations in amounts which do not substantially adversely affect the properties and characteristics desired. Significant amounts of zinc, magnesium and other metal salts and materials, which would complex with the active components of the instant invention are desirably avoided.

Any suitable flavoring or sweetening material may also be employed. Examples of suitable flavoring constituents are flavoring oils, e.g. oil of spearmint, peppermint, wintergreen, sassafras, clove, sage, eucalyptus, marjoram, cinnamon, lemon and orange, and methyl salicylate. Suitable sweetening agents include sucrose, lactose, maltose, sorbitol, xylitol, sodium cyclamate, perillartine, APM (aspartyl-phenyl-alanine, methyl ester), saccharine and the like. Suitably, flavor and sweetening agents may together comprise from about 0.1% to 5% or more of the preparation.

In the preferred practice of this invention an oral composition according to this invention such as a mouthwash or dentifrice containing the described polyphosphate and inhibitor combination in an amount effective to inhibit calculus on dental surfaces is preferably applied regularly to dental enamel, such as every second or third day or preferably from 1 to 3 times daily, at a pH of about 4.5 to about 9, generally about 5.5 to about 8, preferably about 6 to 8, for at least 2 weeks up to 8 weeks or more up to lifetime.

The compositions of this invention can be incorporated in lozenges, or in chewing gum or other products, e.g. by stirring into a warm gum base or coating the outer surface of a gum base, illustrative of which may be mentioned jelutone, rubber latex, vinylite resins, etc., desirably with conventional plasticizers or softeners, sugar or other sweeteners or carbohydrates such as glucose, sorbitol and the like.

The following examples are further illustrative of the nature of the present invention, but it is understood that the invention is not limited thereto. All amounts and proportions referred to herein and in the appended claims are by weight and temperatures are in degrees C. unless otherwise indicated.

EXAMPLE 1

Inhibition of alkaline phosphatase by PVPA and PVMEMA

A reaction mixture is provided containing 0.05 units of $E.$ $Coli$ alkaline phosphatase in a total volume of 0.5 ml, with 100 mM Tris-HCl buffer, pH of 8.0, in which a final concentration of 0.5 mM tetrasodium pyrophosphate is present. The reaction is run at 37° C. after the addition of pyrophosphate for varying amounts of time. The pH of polyvinyl phosphonate, mol. wt. 10,000(PVPA), or of polymeric polycarboxylate, polyvinyl methyl ether/maleic anhydride available from GAF Company as Gantrez S-97(PVME/MA) which has been reported to have a mol. wt. of about 70,000 (by vapor pressure osmometry; but which is determined to have a molecular weight of about 1,090,000 when determined by gel permeation chromatography) is preadjusted to 8.0 prior its being added to the reaction mixture in amount of 0.5%. The reaction is terminated by adding 0.5 ml of 20% cold trichloroacetic (TCA). The amount of orthophosphate released is set forth in the Table 1 below and is calculated as follows:

For each mole of pyrophosphate ion (PPi) hydrolyzed, two moles of orthophosphates are released according to the equation:

On a weight basis, the amount of PPi hydrolyzed (g)=

$$\frac{\text{Molecular Weight } P_2O_7}{2 \times (\text{Molecular Weight } PO_4)}$$

X amount of $PO_4$ generated (g)

TABLE 1

| | Mean Pyrophosphate Hydrolyzed (ug/ml) | | |
|---|---|---|---|
| Reaction Time (min.) | Control Without Inhibitor | + PVME/MA | + PVPA |
| 4.0 | 20.53 | 7.94 | 4.62 |
| 8.0 | 27.04 | 7.92 | 5.28 |

The data show that PVPA inhibits alkaline phosphatase to a greater extent than does PVME/MA.

EXAMPLE 2

Anticalculus Effect In Vivo

Water and the indicated solutions are tested in a rat calculus study with the results shown in Table 2 below:

TABLE 2

| Treatment | Mean Calculus Surface Severity Index ± Standard Deviation | % Change |
|---|---|---|
| A. Water | 61.8 (± 10.4) | |
| B. 6.2% $K_1P_2O_7$, 1% PVPA + 0.24% NaF | 27.8 (± 8.6) | −55% |

It is clear that Treatment B is highly effective against calculus formation in vivo.

The rat calculus study is conducted as follows:

Twenty-one day old male weanling Sprague-Dawley rats are randomized among the treatment groups containing 12 rats per group. The animals are fed calculogenic diet (RC-16) and deionized water, ad libitum, during the entire study. Before initiation of the experimental treatments all animals are inoculated with a suspension of $S.$ $mutans$ (6715) and $A.$ $viscosus$ (OMZ-105-NYL) to stimulate plaque and calculus formation. The rats are treated once daily (excluding weekends) with 0.2 ml of solution using an automatic pipettor.

The experiment is conducted blind; the treatments are coded and unknown to the personnel involved. Rats are sacrificed after 21 days of treatment and the jaws prepared for scoring according to routine methods (SPI TOX 626). Body weights are taken initially and at the time of sacrifice. Calculus on both the maxillary and mandibular quadrants of each rat are evaluated using the method of Briner and Francis reported in "Calcified Tissue Research", Vol. 11, Pages 10–22, 1973, which describes the Calculus Surface Severity Index (CSSI). Statistical analysis of the data are performed using ANOVA plus the Student-Newman-Keuls Test.

EXAMPLE 3

The following toothpastes are prepared:

|  | Parts | | | |
| --- | --- | --- | --- | --- |
|  | A | B | C | D |
| Water (Deionized) | 42.42 | 27.46 | 26.14 | 20.12 |
| Glycerine | 25.00 | 10.00 | 10.00 | 25.00 |
| Sorbitol (70%) | — | 25.00 | 25.00 | — |
| Polyethylene Glycol 600 | — | 3.00 | 3.00 | — |
| Tetrasodium Pyrophosphate | 2.0 | 1.50 | — | — |
| Tetrapotassium Pyrophosphate | — | 4.50 | — | — |
| Sodium Tripolyphosphate | — | — | 6.00 | — |
| Sodium Hexametaphosphate | — | — | — | 6.00 |
| Xanthan | 1.00 | — | — | 1.00 |
| Sodium Carboxyethyl Cellulose | — | 1.20 | 1.20 | — |
| Silica Thickener (Syloid 244) | 3.00 | — | — | 3.00 |
| PVPA | 0.50 | 0.50 | 1.00 | 0.50 |
| Sodium Monofluorophosphate | 0.76 | — | 0.76 | 0.76 |
| Sodium Fluoride | — | 0.24 | — | — |
| Silica containing combined Alumina (Zeo 49B) | 21.50 | — | — | — |
| Colloidal Silica (Zeodent 113) | — | 23.00 | 23.00 | — |
| Calcium Pyrophosphate | — | — | — | 40.00 |
| Sodium Benzoate | 0.50 | 0.50 | 0.50 | 0.50 |
| Titanium Dioxide | 0.50 | 0.30 | 0.30 | 0.30 |
| Sodium Saccharine | 0.30 | 0.30 | 0.30 | 0.30 |
| Flavor | 1.00 | 1.00 | 1.00 | 1.00 |
| Sodium Lauryl Sulfate | 1.20 | 1.20 | 1.20 | 1.20 |
| Sodium Hydroxide (50%) | 0.32 | 0.30 | 0.60 | 0.32 |

EXAMPLE 4

The following mouthwashes are prepared:

|  | Parts | |
| --- | --- | --- |
|  | A | B |
| Ethyl Alcohol | 10.00 | 10.00 |
| Glycerine | 10.00 | 10.00 |
| Sodium Saccharine | 0.03 | 0.03 |
| Block Copolymer Pluronic F 108 | 2.00 | 2.00 |
| Tetrasodium Pyrophosphate | 2.00 | 1.00 |
| Tetrapotassium Pyrophosphate | — | 1.00 |
| Disodium Pyrophosphate | — | 0.10 |
| PVPA | 0.05 | 0.05 |
| Sodium Monofluorophosphate | 0.15 | 0.15 |
| Flavor | 0.40 | 0.40 |
| Water | Q.S. to 100.00 | Q.S. to 100.00 |

EXAMPLE 5

Lozenges

| Sugar | 78-98 |
| --- | --- |
| Corn syrup | 1-20 |
| Flavor oil | 0.1-1.0 |
| Tablet lubricant | 0.1-5 |
| Polyphosphate | 0.1-5 |
| PVPA | 0.05-3 |
| NaF | 0.01-0.05 |
| Water | 0.01-0.2 |

EXAMPLE 6

Chewing Gum

| Gum base | 10 to 50 |
| --- | --- |
| Binder | 3 to 10 |
| Filler (sorbitol, mannitol or combination thereof) | 5 to 80 |
| Artificial sweetener | 0.1 to 5 |
| Polyphosphate | 0.1 to 5 |
| PVPA | 0.1 to 1.0 |
| NaF | 0.01-0.05 |
| Flavor | 0.1 to 5 |

The invention has been described with respect to certain preferred embodiments and it will be understood that modifications and variations thereof obvious to those skilled in the art are to be included within the purview of this application and the scope of the appended claims.

We claim:

1. An oral composition which inhibits the transformation of amorphous calcium phosphate to HAP crystal structure normally associated with calculus, comprising, in an orally acceptable vehicle an effective anticalculus amount of about 0.1-7% by weight of at least one linear molecularly dehydrated polyphosphate salt as essential anticalculus agent, and, an effective amount of inhibitor against enzymatic hydrolysis of said agent in saliva of about 0.05% up to about 4% by weight of a synthetic anionic polyvinyl phosphonate, having recurring groups

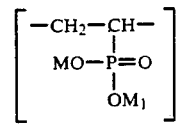

and average molecular weight of about 1,000 and greater; and wherein M and $M_1$ are hydrogen, alkali metal or ammonium, and wherein M and $M_1$ are the same or different.

2. The oral composition claimed in claim 1 wherein said polyvinyl phosphate has a molecular weight of about 1,000 to about 1,000,000.

3. The oral composition claimed in claim 1 wherein said polyvinyl phosphonate has a molecular weight of about 6,000 to about 100,000.

4. The oral composition claimed in claim 2 wherein said polyvinyl phosphonate is present in amount of about 0.05-3% by weight.

5. The oral composition claimed in claim 4 wherein said amount of polyvinyl phosphonate is about 0.1-2% by weight.

6. The oral composition claimed in claim 1 wherein said polyphosphate salt is selected from the group consisting of hexametaphosphates, tripolyphosphates, pyrophosphates and mixtures thereof.

7. The oral composition claimed in claim 1 wherein said polyphosphate salt is selected from the group consisting of tetrasodium pyrophosphate, tetrapotassium pyrophosphate and mixtures thereof.

8. The oral composition claimed in claim 1 wherein said polyphosphate salt is present in amount of about 4.3-7% by weight and is a mixture of tetrapotassium pyrophosphate and tetrasodium pyrophosphate, with the amount of tetrapotassium pyrophosphate being predominant over the amount of tetrasodium pyrophosphate.

9. The oral preparation claimed in claim 1 wherein said polyphosphate salt is tetrasodium pyrophosphate which is present in amount of about 0.1-2% by weight.

10. The oral composition claimed in claim 1 wherein said polyphosphate salt is a tripolyphosphate.

11. The oral composition claimed in claim 1 wherein said polyphosphate salt is a hexametaphosphate.

12. The oral composition claimed in claim 1 wherein said vehicle comprises about 10%-90% by weight of a liquid vehicle comprising water and humectant and about 0.1-10% by weight of a gelling agent and wherein there is present about 10-75% by weight of a dentally acceptable water-insoluble polishing agent; said oral composition being a toothpaste.

13. The oral composition claimed in claim 12 wherein said polishing agent is a siliceous polishing agent.

14. The oral composition claimed in claim 1 wherein said vehicle is about 70-99.9% by weight of a water-alcohol mixture, the weight ratio of water to alcohol being from about 1:1 to about 20:1; said oral composition being a mouthwash.

15. The oral composition claimed in claims 1 wherein a fluoride-ion source is present in amount sufficient to supply a non-toxic amount of about 25-2,000 ppm of fluoride ions, as an anticaries agent and as a further inhibitor against enzymatic hydrolysis of said essential anticalculus agent.

16. The oral composition claimed in claim 15 wherein said fluoride-ion source is selected from the group consisting of alkali metal fluoride and alkali metal monofluorophosphate.

17. The oral composition claimed in claim 16 wherein said fluoride-ion source is sodium fluoride.

18. A method of inhibiting dental calculus comprising applying to teeth a calculus-inhibiting amount of the oral composition of claim 1 said oral composition having a pH of about 4.5 to about 9.

19. A method of inhibiting dental calculus comprising applying to teeth a calculus-inhibiting amount of the oral composition of claim 15, said oral composition having a pH of about 4.5 to about 9.

* * * * *